United States Patent [19]

Berry

[11] Patent Number: 5,462,163

[45] Date of Patent: Oct. 31, 1995

[54] HOLDER FOR SHARP MEDICAL INSTRUMENTS WITH INDIVIDUAL ANGULARLY PRESENTED ENCASEMENTS

[75] Inventor: Arnold J. Berry, Atlanta, Ga.

[73] Assignee: Emory University, Atlanta, Ga.

[21] Appl. No.: 318,563

[22] Filed: Oct. 4, 1994

Related U.S. Application Data

[63] Continuation of Ser. No. 45,511, Apr. 8, 1993, abandoned.

[51] Int. Cl.[6] ............................ B65D 83/10; B65D 69/00
[52] U.S. Cl. ........................ 206/370; 206/571; 206/443; 211/70.6
[58] Field of Search ..................... 206/570, 571, 206/363–370, 372, 373, 443, 446; 211/60.1, 70.6

[56] References Cited

U.S. PATENT DOCUMENTS

| | | | |
|---|---|---|---|
| 1,184,494 | 5/1916 | Sorensen | 206/370 X |
| 1,822,487 | 9/1931 | Hill | 206/370 |
| 2,635,031 | 4/1953 | Erhardt | 211/60.1 X |
| 3,239,069 | 3/1966 | Hollins | 211/60.1 |
| 3,301,619 | 1/1967 | Mead | 206/373 X |
| 4,212,392 | 7/1980 | McKenzie | 206/571 |
| 4,412,618 | 11/1983 | La Conte | 206/373 X |
| 4,848,587 | 7/1989 | Nipp | 206/571 |

FOREIGN PATENT DOCUMENTS

| | | | |
|---|---|---|---|
| 672540 | 10/1963 | Canada | 206/370 |
| 4115251 | 11/1992 | Germany | 211/70.6 |

*Primary Examiner*—Bryon P. Gehman
*Attorney, Agent, or Firm*—Hopkins & Thomas; James W. Kayden

[57] ABSTRACT

A self-contained medical procedure kit and stand having a tray and receptacles for medical instruments is provided in such a way as to safely and easily allow a health care worker to remove sterile medical instruments from the kit, replace and retrieve the instruments for reuse during a procedure, and dispose of the medical instruments after use. The stand facilitates the medical procedure and is designed to greatly reduce the possibility of needle-stick injuries because it maintains the medical instruments in an angled, accessible position and encases the sharp ends of instruments, syringes and the like.

14 Claims, 4 Drawing Sheets

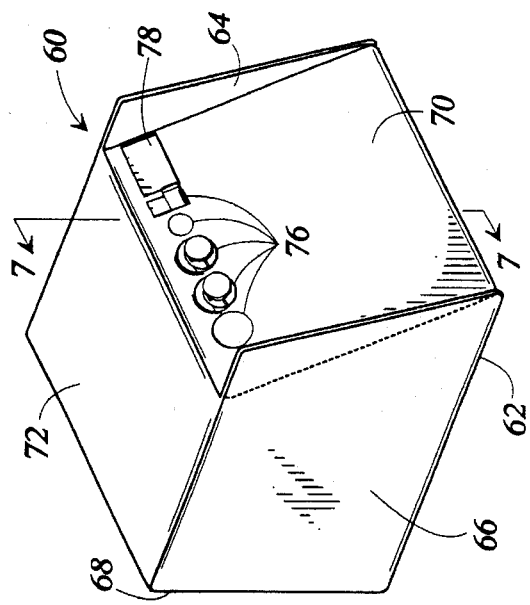
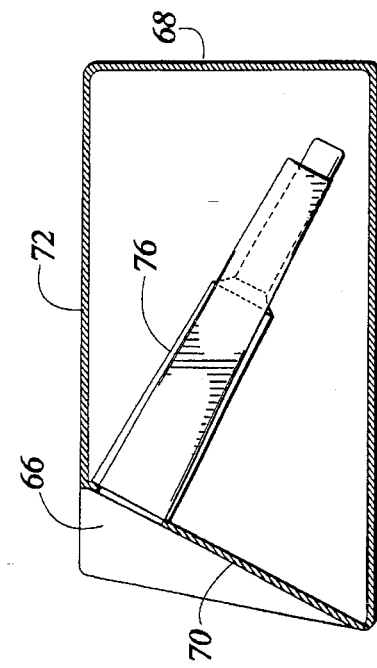
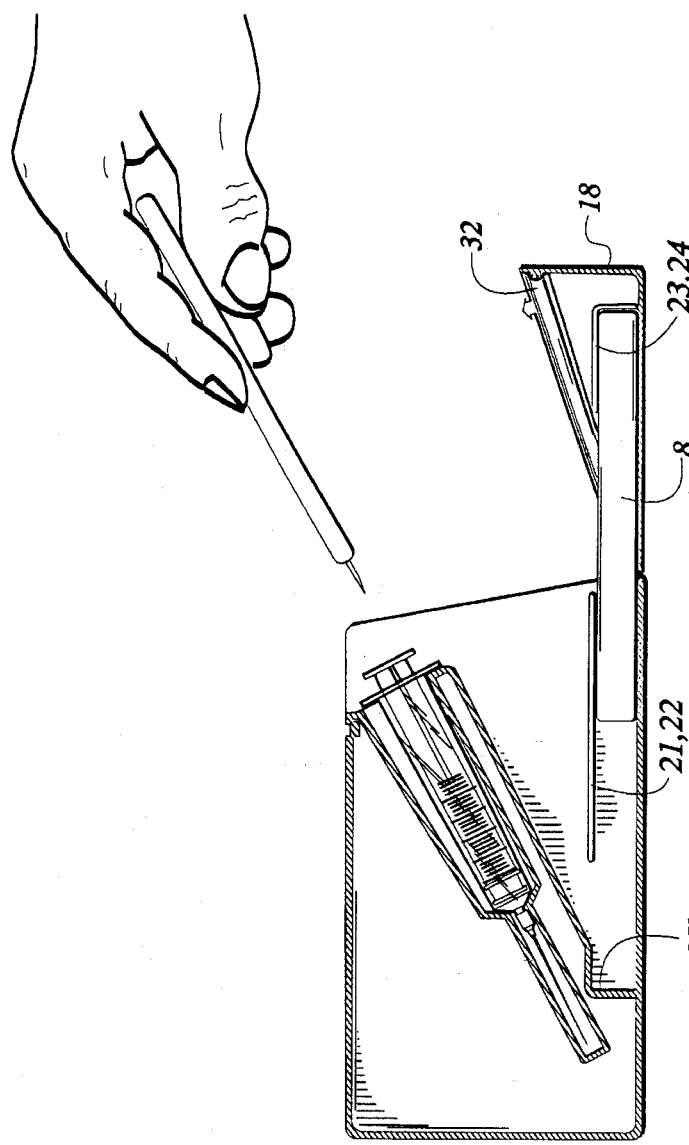
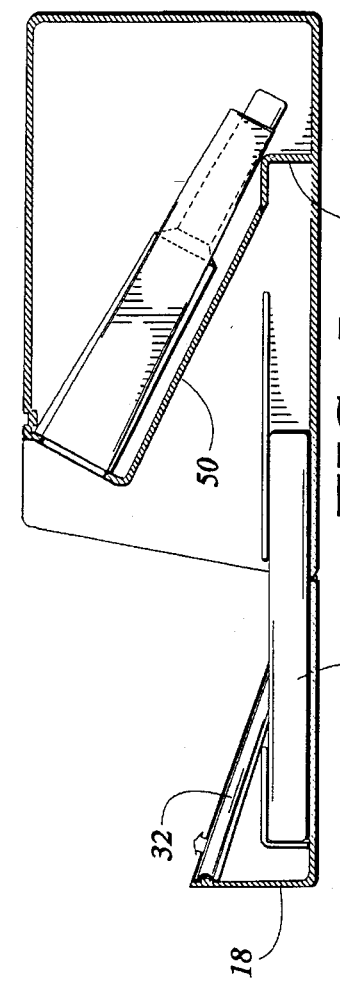

HOLDER FOR SHARP MEDICAL INSTRUMENTS WITH INDIVIDUAL ANGULARLY PRESENTED ENCASEMENTS

This is a continuation of application Ser. No. 08/045,511 filed on Apr. 8, 1993, now abandoned

FIELD OF THE INVENTION

This invention is in the field of devices useful for the safe packaging, intermittent storage, and disposal of needles and other sharp medical instruments. In particular, this invention relates to an improved holder for such instruments and a medical procedure tray which facilitates the safe use and disposal of such instruments.

BACKGROUND OF THE INVENTION

Health care workers are frequently exposed to a patient's blood or body fluids during the course of a medical procedure. In particular, health care workers are exposed to sharp medical instruments (sharps) that have had contact with a patient's blood or body fluid. If a medical instrument that has come in contact with a patient's blood or body fluids is not properly maintained and handled during and after a procedure, the health care worker may be infected through contact with the medical instrument.

Needle stick or puncture wound injuries are very common ways in which health care workers are infected with a patient's blood or fluid borne pathogens. In fact, accidental needle sticks and medical sharp caused injuries pose the most significant risk to health care workers for occupational transmission of various blood borne pathogens such as, for example, hepatitis B, hepatitis C, and human immunodeficiency virus (HIV).

In an effort to reduce the health care worker's high risk of exposure to infectious materials, the Occupational Safety and Health Administration (OSHA) of the U.S. Department of Labor has developed standards that are designed to minimize or eliminate the health care worker's exposure to blood or body fluid borne pathogens. Requirements for disposal of contaminated sharps include puncture resistant and liquid-proof containers, positive sealing ability both before and after use, specified colors, and a biohazard designation symbol. (Occupational Exposure to Blood-Borne Pathogens: Final Rule 29 C.F.R. 1910.1030.) Similar provisions are in force in other countries.

Part of this strategy is to reduce the health care worker's exposure to infectious materials and needle sticks by removing the hazards from the health care worker's environment without requiring extra actions on the part of the health care worker. Examples of such equipment include equipment designed to either eliminate the use of needles or provide passive protective mechanisms for needles or sharp devices.

Although there has been an emphasis on and general acceptance of the use of this type of protective equipment by health care workers having contact with infectious material, incorporation of needle-less or protected needle devices in clinical practice has been very limited because their usage is often quite cumbersome.

Several patents have issued that attempt to provide the health care worker with a safe apparatus for using needles, syringes, and other medical sharps. For example, U.S. Pat. No. 5,047,019 to Sirock and U.S. Pat. No. 5,092,462 to Sagstetter et al. teach devices for the safe removal and disposal of sharps from medical instruments. However, neither Sincock nor Sagstetter et al. teach a device that provides for safe needle or sharp disposal that does not require an additional effort on the part of the health care worker. U.S. Pat. No. 5,097,963 to Chernosky, et al. teaches a rack for temporarily storing surgical instruments during surgery. The rack has a series of individual grooves, each with an inclined bottom surface to incline the instrument toward its "user's" end. The sharp end of the instrument is disposed in the groove, and the grooves are separated by partition walls.

In addition, U.S. Pat. Nos. 5,099,992 to Heimreid and 5,024,666 to Pituch teach devices that allow the safe and user friendly removal and storage of needles and medical sharps. However, neither Heimreid or Pituch teach an apparatus that provides a one-unit device that sterilely houses needles and medical sharps prior to their usage and provides for their safe disposal after use.

Although others have taught pre-sterilized medical procedure kits (see U.S. Pat. Nos. 5,031,768 to Fisher; 4,522, 302 to Paikoff), these kits do not allow the health care worker to readily remove and replace ready-for-use instruments, maintaining the instruments in an easily accessible position, and provide for the safe and easy disposal of the contaminated instrument.

With the above-described requirements for safe use and disposal in mind, it is therefore an object of the present invention to provide a device and medical procedure kit for the safe packaging, intermittent storage, and disposal of sharp medical instruments sterilely packaged self-contained medical procedure kit or tray. The device provides that an instrument may be readily removed, replaced and retrieved; and may also function as a puncture-resistant locking receptacle for discarding contaminated medical instruments.

SUMMARY OF THE INVENTION

The present invention comprises in one embodiment a holder for the safe packaging, intermittent storage, and disposal of needles and other sharp medical instruments. The device has a bottom surface, right and left sides, and front and back ends. A top portion may extend angularly from the front and toward the back end to present the instruments in a position easily accessible to the health care worker while supporting the instrument in an essentially upright position throughout the length thereof. One or more discrete encasements parallel with the sides and perpendicular to the angled portion are provided for holding the various instruments. The encasements may have bottoms for supporting the instruments or may be "bottomless" to prevent retrieval of spent instruments and the like.

In another embodiment, the invention comprises a self-contained medical procedure kit having a tray and a plurality of substantially straight, angularly presented encasements for individually holding medical instruments such as syringes, scalpels and other medical sharps. When packaged, the kit and its containments are sterilized and sealed so as to maintain the instruments contained therein in a sterile environment prior to use. In use, the seal of the kit is broken, and the lid is opened such that the sterile medical instruments contained therein are exposed in a safe, ready-to-use position, which is normally an angled position directed toward the user. During a procedure, the tray and angled encasements allow the user to safely and easily remove, replace, and retrieve an instrument. After completion of a procedure, the outer housing or box along with the encasements serves as a puncture-resistant, leak-proof disposal container.

The medical instruments located in the receptacles on the angled panel are oriented toward the user at an angle to allow the user to grasp the instrument only by the instruments "safe end", or "user's end", which is the end of an instrument that does not make contact with a patient. Because each needle and sharp device can have an individual receptacle, it is not necessary to recap the individual needle or device during or after use. The receptacles also protect the sharps when they are not in use. During a procedure, the cover or cap of the housing can be used as a work surface for placing items without needles or sharps (i.e., drug vials, gauze . . . ). At the bottom of the housing is also provided a means for maintaining the cover in an open, horizontal position.

The cover of the housing is hinged so that it can be closed after use to create a completely closed puncture-resistant and leak-proof container for disposal of the used needled and sharp devices contained therein. The sides of the cover and housing are therefore provided with a means for permanently sealing the procedure tray after its use.

Other medical procedure kits which incorporate angularly presented encasements for individually holding instruments such as syringes, scalpels, and other medical sharps are also possible. Such kits, for example, may include a hinged cover or separate tray component as discussed hereinabove. Such kits may; however, also include recessed areas of various dimensions and shapes in their front or top surfaces suitable for holding non-sharp items useful in medical procedures. These items may include antiseptics, swabs, drug vials, etc. The recessed areas may be present whether or not a hinged cover or tray is provided.

This invention provides for a holder or stand that contains ready-to-use medical instruments and additionally provides for the ready removal, replacement and retrieval of medical instruments during a medical procedure. The invention further provides a self contained procedure kit that eliminates the need for a health care worker to handle or carry contaminated medical instruments or medical sharps to a separate container after use for disposal.

BRIEF DESCRIPTION OF THE DRAWINGS

FIG. 4 is a cross-sectional view showing a health care worker using the self-contained procedure kit while it is open, the view being taken on line 4—4 of FIG. 1;

FIG. 5 is a cross-sectional view of the self-contained procedure kit in an open position; the view being taken on line 5—5 of FIG. 1;

FIG. 6 is a perspective view of a holder for sharp medical instruments in accordance with the present invention;

FIG. 7 is a cross-sectional view of the alternate embodiment shown in the preceding figure, the section being taken on line 7—7 of FIG. 6.

DETAILED DESCRIPTION OF THE PREFERRED EMBODIMENT

Figure 1:
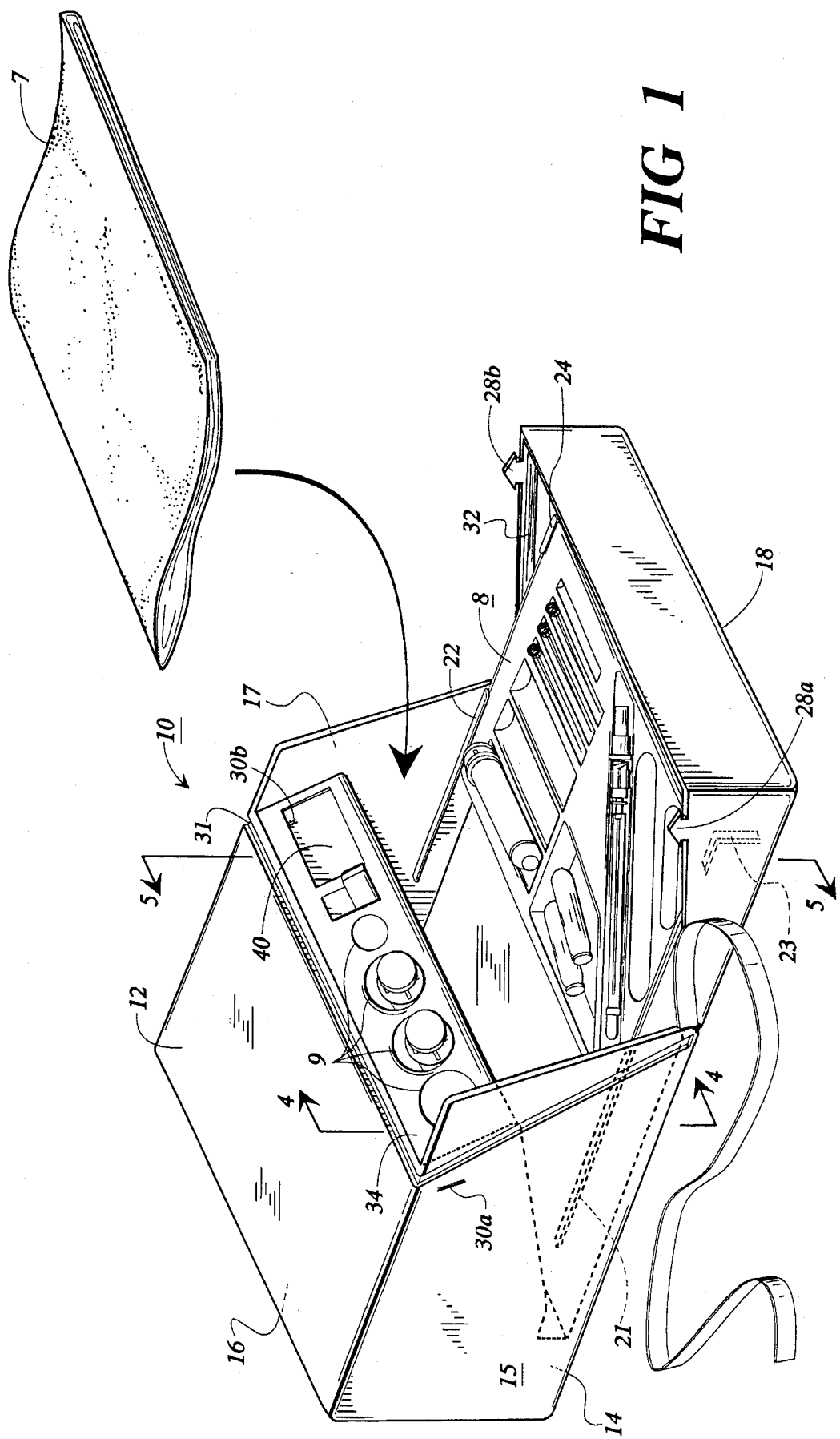
FIG. 1 is a perspective view of one embodiment of the invention.

The self-contained procedure kit of the present invention is generally designated by the reference numeral 10 in the drawings. Referring now to FIG. 1, the self-contained kit 10 has top surface 12, bottom surface 14, back surface 16, left side 15, right side 17, and cover 18.

As shown in FIG. 1, when the cover 18 is maintained in an open position, tray 8 is visible. Tray 8 may be configured in a plurality of different embodiments that are specific to a certain medical procedure. For example, trays are provided for catheterization procedures, intravenous procedures, etc. and the instruments and medicaments provided therein will also vary depending on the patients, i.e. adults, children, male, female, etc. The kit shown in FIG. 1 is designed to illustrate what a kit of this type might look like when it is initially opened for use. The present invention is illustrated essentially as a ready-to-use procedure kit. However, the invention also contemplates the housing and the angled receptacle or receptacles provided as a separate item or in conjunction with a prior art medical procedure kit. In this manner, the invention serves as basically a holder or stand and a protective device for the health care worker, providing conveniently angled receptacles for individually housing medical sharps taken from a conventional tray. Throughout this application, the terms receptacle and encasement are used interchangeably to describe the holding means having openings on the angled panel. The receptacles are normally oriented at approximately a 45° (forty-five degree) angle relative to the vertical, although other similarly presented angles are contemplated as being within the scope of the present invention. It is important to note, however, that the instruments in the receptacles are essentially surrounded and therefore shielded from one another. This prevents cross-contamination where such might be a problem, but furthermore provides the surrounding walls as means for securably supporting the instruments in their angled position. It can also be seen that the receptacles are elongated so as to shield or contain most of the instrument within the receptacle as opposed to those prior art devices which shield only the tip of the instrument.

The drape 7 may be included in many kits as a sterile barrier for use in medical procedures. In prior art kits, substantially all of the contents are disposed in compartments in the tray itself. With the present invention, while some of the instruments, vials, etc. are disposed in the tray, all of the sharps, scalpels, needled syringes, etc., are disposed in the individual angled compartments 9, as discussed in detail hereinbelow. The instruments shown in the kit in FIG. 1 are for illustrative purposes and are not to be construed as limiting in any sense.

During a medical procedure-in which the present invention is used, it is desirable to maintain the cover 18 in a fully-opened position. As such, securing means are provided for maintaining the open orientation. As an example of such an embodiment, FIGS. 4 and 5 show tray 8, slidably mounted in a horizontal position below first mils 21 and 22 and second rails 23 and 24. The combined rails and their engagement with the tray maintain the cover 18 in an open position. Other securing means, i.e. struts, clamping means, etc. may also be used to maintain the cover in an open position and their inclusion as such will be readily apparent to those of ordinary skill in the art. Cover 18 also has locking means 28a and 28b. When the self-contained kit 10 is in an after-use closed position, locking tabs 28a and 28b permanently engage slots 30a and 30b such that the cover can not be reopened. As the container must be sealed against leakage when the particular medical procedure is finished, the housing is provided with a groove means 31 that accepts a bead 32. The groove is formed in each side of the housing and the top surface. The bead is disposed on each inner side and on the inner top surface of the cover. When the cover is closed, the bead engages the groove to form a leak-proof seal. As an alternate embodiment, the bead, the groove, or both may be provided with an adhesive sealant means, such as a silicone-based adhesive, to further guard against leakage.

Panel 34 is angled from top 12 such that the health care worker will have convenient, safe, and ready access to the medical instruments housed in the angled receptacles 9. For some procedure kits or housing means only a single receptacle may be provided, depending on the ultimate use. In most cases, however, a plurality of receptacles are provided. The receptacles may be, but are not necessarily made of the same puncture-resistant material as the housing, and are completely enclosed except for the openings on panel 34. The panel itself may also be formed from the same material as the housing or it may be transparent or at least translucent so the health care worker can see the instruments, their state, i.e. full, empty, color-coding etc. Pursuant to current OSHA standards, only the outer housing must be puncture resistant and meet the requisite standards as to color coding, warning symbols, etc. It should also be noted that the receptacles may be provided as housings for non-sharp instruments also, such as, for example, an elongated receptacle for a catheter or other instrument.

Figure 2:
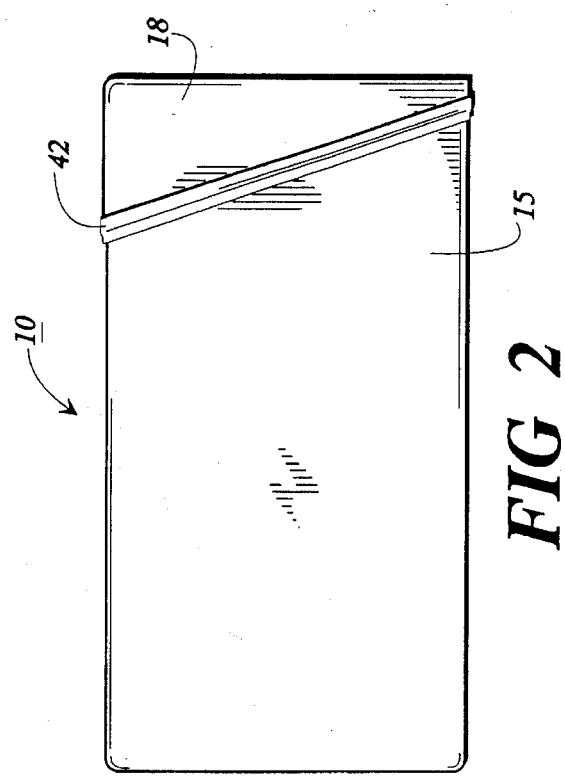
FIG. 2 is a side elevational view of the sterilely sealed self-contained procedure kit prior to its use.

Referring now to FIG. 2, the self-contained kit 10 is shown in a closed position, prior to being first opened. A sealer on tape 42 seals and connects cover 18 to left side 15, top 12 and right side 17. To open the self-contained procedure kit the user must first remove sealer 42 so that cover 18 may be moved to an open position.

Figure 3:
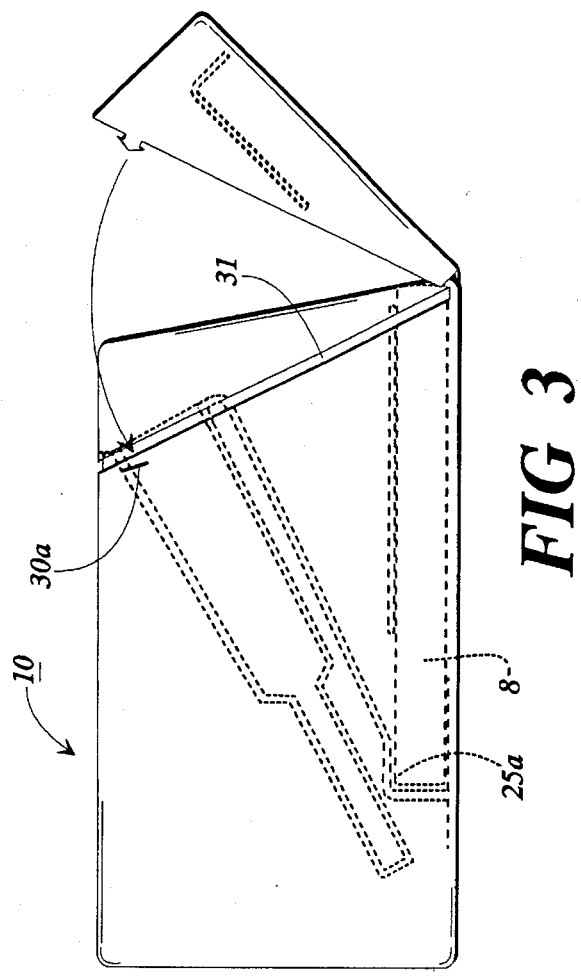
FIG. 3 is a side elevational view of the self-contained procedure kit being closed.

Referring now to FIG. 3, it can be seen that when tray 8 is disposed in its fully inserted position an angled abutment 25a on one side and 25b on the other side, in combination with the closed cover 18, keep the tray from moving inside the housing when the kit is sealed and during sterilization and transport.

In the use and operation of the present invention, the user must first orient the self-contained kit 10 so that top surface 12 is facing upward, as indicated by a decal or other means. The user must next proceed to remove sealer 42 and move cover 18 into an open position. When cover 18 is moved into an open position, the ready-to-use medical instruments are accessible. In addition, the user will see tray 8 in an inward or stored position covered by drape 7. For using the tray, the drape is removed and the tray is moved to the outward position shown in FIGS. 1, 4 and 5. When the tray is in its outward position it engages both first rails 21 and 22, and second rails 23 and 24 so as to maintain cover 18 in an open position.

As noted hereinabove, the tray itself may not be provided in the housing, but as a separate item. Similarly, the tray may be provided as a sealed, sterile item within a non-sterile housing, depending on the particular use for which the present device is designed.

The user or health care worker can now use the self-contained kit for the particular procedure to be performed. For example, the user may easily remove the angularly presented medical instruments housed in receptacles 9. The user can also remove and use additional instruments, drug vials, etc. from the tray as needed.

During the procedure, the angularly presented compartments or receptacles facilitate and therefore encourage the user to remove, replace and retrieve the medical instruments from their respective angularly presented receptacles, thereby greatly reducing the risk of accidental needle-stick injuries. It is common for an instrument to be used more than once, and the present invention disposes the instrument in a much better position for use than if the instrument were simply set down in the tray.

After the procedure is over, or after an instrument's particular use is completed, the user simply replaces the medical instrument(s) in its original receptacle. The tray is then moved from its outward position to its inward position. Cover 18 is then moved to its closed position such that locking means 28a and 28b engage reciprocating locking means 30a and 30b, respectively. Bead 32 is also engaged in groove 31, sealing the container against leakage. As noted, an adhesive means on the bead, groove, or both may also be employed as an additional seal.

The self-contained puncture-resistant housing is now in a post-use sealed state that is also leak-proof and tamper-proof. Because of the nature of the material used for the housing, the enclosed contaminated medical instruments are sealed such that they can not stick, puncture, cut or harm a health care worker. The sealed self-contained housing is thereafter discarded according to Federal or State guidelines.

As an added feature of the present invention, one or more of the receptacles, such as receptacle 40 is converted from a closed receptacle to an open-ended opening. Such an opening allows the user to use the interior of the housing 10 to discard medical items such as gauze, sutures, bandages, drug vials or the like by merely pushing the device to be discarded through the opening. In this embodiment a barrier wall 50 is provided, the barrier wall being connected to the angled panel and end portions 25a and 25b to define the box's inner cavity. This inner cavity is only accessible via its opening on the angled panel, as shown in FIGS. 3 and 5.

FIGS. 6 and 7 illustrate an alternate embodiment of the present invention. In this embodiment, the device 60 is similar to the first described embodiment in that the angular presentation of the instruments, their essentially complete encasement before or between uses, and the open-ended discard or disposal opening or openings are provided as previously described. Omitted are the tray and instruments, and the sealable cover. This embodiment of the invention is primarily designed for use with existing procedure trays that are supplied in essentially complete packages for individual medical procedures, i.e. a vessel catheterization kit.

As shown in FIGS. 6 and 7, the alternate embodiment serves as a stand 60 for medical instruments and the like, having a base 62, right and left sides 64 and 66, respectively, and, front and back panels 68 and 70, respectively. A top portion 72 extends perpendicularly from the back panel toward the front or face panel 70. The face panel slopes angularly downward from the top portion to meet the base 62.

The configuration of the encasements 76 may vary but, in general, as shown in FIG. 7, they have sufficient depth to substantially surround the syringe, scalpel, etc. In addition, an aperture 78, which communicates with the interior of stand 60, is provided for discarding spent instruments and is designed such that the spent instrument cannot be retrieved. The present invention further contemplates that the encasement or group of encasements be separately provided and thus removable from stand 60 or from the other holders or kits described herein. Means for receiving and releasing holding the encasements as well as a sealable cover are provided in such an embodiment. For example, track means may be provided in the stand to angularly receive the encasement module. The sealable cover would provide a leakproof enclosure and the entire module would be comprised of puncture-proof material for safe disposal where indicated.

Figure 8:
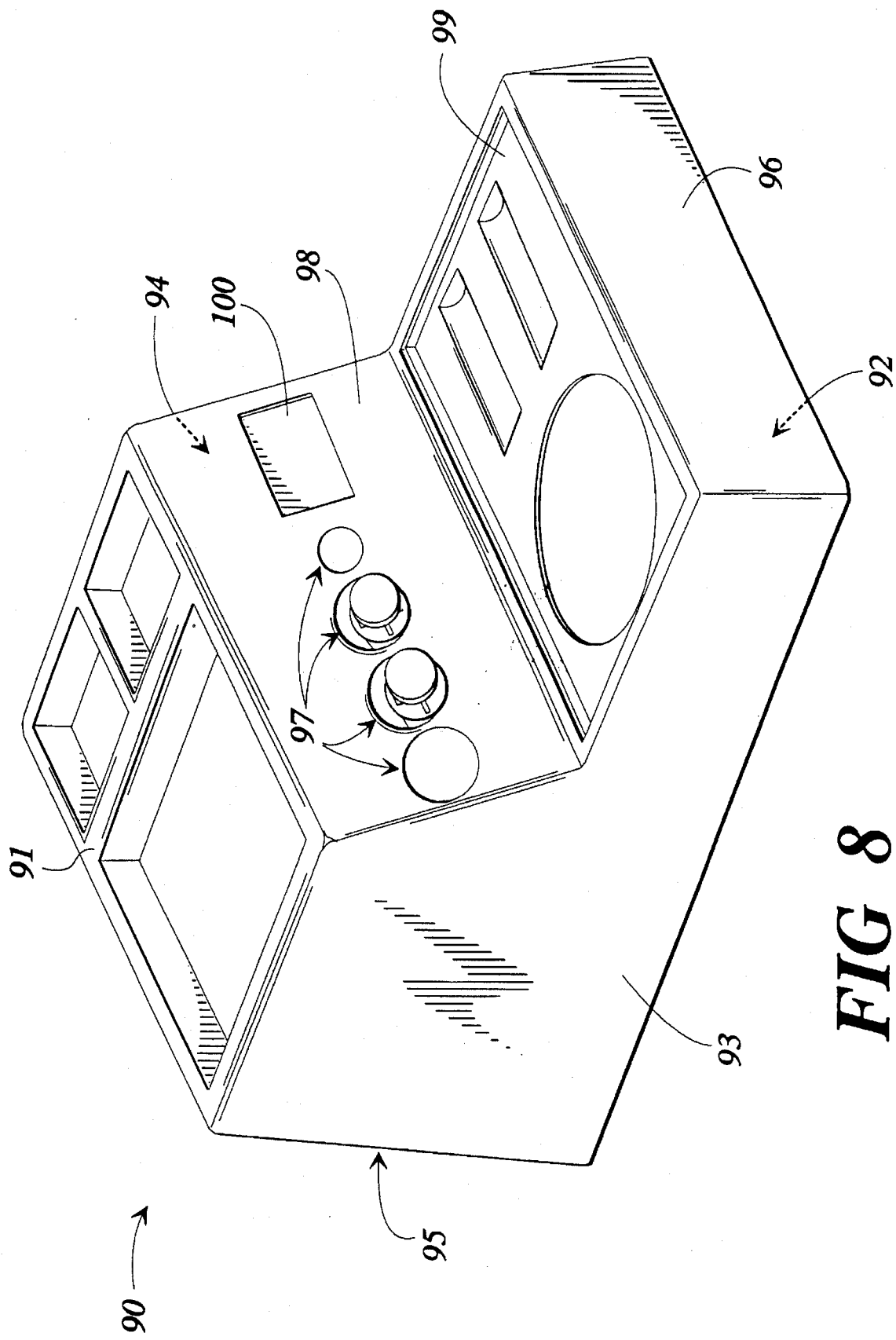
FIG. 8 is a perspective view of a procedure kit in accordance with the present invention.

The alternate embodiment of the invention shown in FIG. 8 is generally designated as reference numeral 90 in the drawing. Stand 90 is designed for use as essentially an instrument and supplies holder, supply, storage, and disposal means.

Referring to FIG. 8, the stand has top panel 91, bottom surface 92, left side 93, right side 94, back surface 95 and front lower surface 96. Panel 98 extends angularly from top panel 91 and joins front middle panel 99. The top surface 91 extends perpendicularly from the back surface 95. The front upper panel 98 is angled from the top panel, 96, to the front middle panel, 99, similar to the embodiments above and can contain similar individual receptacles or encasements, 97, for storage, disposal, etc. and a similar open-ended encasement, 100.

The front middle panel, 99, extends perpendicularly from the front lower surface, 96. The front middle panel contains various receptacles for non-sharps, i.e. drug vials, swabs, instruments, etc. as needed for the procedure for which the particular kit is designed. In addition, the top surface, 91, contains various receptacles and serves as a prep tray for holding gauze, antiseptics, swabs, medicaments, etc.

While the present invention has been described in accordance with the preferred embodiments of the various figures, it is to be understood that other similar embodiments may be used or modifications and additions may be made to the described embodiment for performing the same functions of the present invention without deviating therefrom. The present invention should therefore not be limited to any single embodiment but rather construed in breadth and scope in accordance with the recitation of the following claims.

I claim:

1. A holder for the safe packaging, intermittent storage and disposal of needles and sharp medical instruments comprising a puncture-proof container means for use in storing, holding and disposing of needles and sharp medical instruments, said container means having a sealable cover with sealing means associated therewith, said sealing means comprising means for ensuring that no liquid can enter or exit said holder when said cover is closed and such that said container means and any contents therein can be sealed, sterilized, and remain sterile until said cover is unsealed and opened, said container means also having a bottom surface, a right side, a left side, a back panel and a top panel which comprises a portion of said cover, said top panel extending perpendicularly from said back panel, and including a face panel which slopes toward the bottom surface; and one or more discrete encasements each having a bottom end and being disposed parallel to said left and right sides and perpendicular to said face panel with an aperture on said face panel in communication with each encasement for receiving and holding needles, devices with needles and sharp instruments within said each encasement with the sharp or pointed end directed toward said bottom end, each encasement being disposed at an angle relative to vertical and between 0° and 90° for presenting received needles and sharp medical instruments at an angle oriented toward a user.

2. The holder of claim 1 wherein the sealing means is a bead on the cover and a groove on the housing so that when the bead engages the groove a leak proof seal is formed.

3. The holder of claim 1 and further comprising a sealer tape which seals and connects the cover to the housing and which must be removed before the cover can be removed from the housing.

4. A self contained medical procedure kit comprising a housing having a bottom surface, a right side, a left side, a front end, a front panel, and a top surface; an angled panel between and connected to said top surface and front panel and perpendicularly positioned between said left and right sides and having one or more apertures, one or more encasements respectively communicating with said one or more apertures each encasement and having a bottom end such that said one or more encasements are suitable for receiving needles, devices with needles and sharp instruments and preventing received needles, devices, and instruments from contacting one another, and where said one or more encasements are defined by the interior of said housing so that used items may be disposed of through said one or more encasements into the interior of said housing for making the disposed used items inaccessible; and recessed areas incorporated in said top surface and front panel having different dimensions and shapes suitable for storing various non-sharp items useful in medical procedures.

5. A self-contained medical procedure kit comprising:

a housing having a top surface, a bottom surface, a right side, a left side, a front end and a back end;

a cover comprising said front end, a portion of said right and left sides and a portion of said top surface, said cover also having a plurality of sides sealable to said housing; and being movable from a closed position to an open position;

sealing means for sealing said cover to said housing when said cover is in its closed position for preventing leakage of fluids or solids from inside said housing to outside said housing and for maintaining sterility of said kit before it is initially opened;

an angled panel connected to said top surface and perpendicularly positioned between said left and right sides and having one or more apertures, one or more encasements respectively communicating with said one or more apertures and suitable for receiving needles, devices with needles, and sharp instruments, and one or more encasements in addition communicating with the interior of said housing; and said kit is comprised of material which is sterilizable.

6. The self-contained kit as defined in claim 5, further comprising a locking means for locking said cover in a closed position after said housing has been opened.

7. The self-contained kit as defined in claim 5, further comprising a slidable tray disposed within said housing and an elongated longitudinally disposed first guide means positioned on the inside surface of one or more of said sides above said slidable tray for preventing said tray from moving vertically within said housing.

8. The self-contained kit as defined in claim 7, further comprising a second guide means positioned on the side portions comprising said cover such that when said cover is in its open position said second guide means prevents said tray from moving vertically.

9. The self-contained kit as defined in claim 7, further comprising an end portion on the inside of one or more of said sides perpendicular to said first guide means, such that said tray is prevented from moving within said housing beyond said end portion.

10. The self-contained kit as defined in claim 5, wherein said one or more encasements may each be circular, rectangular or square.

11. The self-contained kit as defined in claim 5, wherein said one or more encasements are each elongated.

12. A self-contained medical procedure stand for the holding, removal, replacement, retrieval and disposal of medical instruments, comprising:

a housing portion and a cover portion having an open position and a closed position, wherein said cover portion and said housing portion form an enclosure when said cover portion is in its closed position;

sealing means having a bead means and a receiving means for said bead means for sealing said cover portion to said housing portion when said cover is in its closed position for preventing leakage of fluids or solids from inside said housing to outside said housing and for maintaining sterility of said enclosure before it is initially opened;

said housing portion having a back end surface, a top surface, a bottom surface and two side surfaces;

a panel angled from said top surface and between said side surfaces;

at least two encasements each having an opening in said panel wherein one of said encasements is further defined by the interior of said housing portion;

a slidable tray located on the inside of said bottom surface such that said tray may slidably move between said housing portion and said cover portion when said cover portion is in its open position; and a reciprocal locking means that locks said cover portion to said housing portion when said cover portion is in its closed position.

13. The self-contained stand as defined in claim 12, wherein said housing portion is made of a puncture proof material.

14. The self-contained stand as defined in claim 12, wherein said locking means functions to lock said housing portion to said cover portion after said cover portion has been opened for the first time.

* * * * *